US008852415B2

(12) United States Patent
Runge

(10) Patent No.: US 8,852,415 B2
(45) Date of Patent: Oct. 7, 2014

(54) SENSOR ELEMENT HAVING LIMITING CURRENT CALIBRATION FREE OF CRACKS

(75) Inventor: Henrico Runge, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 1364 days.

(21) Appl. No.: 12/508,865

(22) Filed: Jul. 24, 2009

(65) Prior Publication Data

US 2010/0018860 A1 Jan. 28, 2010

(30) Foreign Application Priority Data

Jul. 25, 2008 (DE) ......................... 10 2008 040 731

(51) Int. Cl.
*G01N 27/406* (2006.01)
*G01N 27/407* (2006.01)

(52) U.S. Cl.
CPC .......... *G01N 27/4072* (2013.01); *G01N 27/406* (2013.01)
USPC ........... 204/424; 204/425; 204/426; 204/427; 73/23.31; 73/23.32

(58) Field of Classification Search
CPC .................................................... G01N 27/406
USPC ....................... 204/424–429; 73/23.31–23.32
See application file for complete search history.

(56) References Cited

U.S. PATENT DOCUMENTS

| | | | |
|---|---|---|---|
| 6,645,360 B1 * | 11/2003 | Eisele et al. | 204/426 |
| 2002/0197120 A1 * | 12/2002 | Newmark | 408/72 B |
| 2006/0151466 A1 * | 7/2006 | Diehl | 219/448.11 |
| 2007/0108049 A1 * | 5/2007 | Wahl et al. | 204/424 |

FOREIGN PATENT DOCUMENTS

| | | |
|---|---|---|
| DE | 103 45 141 | 4/2005 |
| WO | 2007/104621 | 9/2007 |

* cited by examiner

*Primary Examiner* — Bach Dinh
(74) *Attorney, Agent, or Firm* — Kenyon & Kenyon LLP

(57) ABSTRACT

A sensor element for determining at least one physical property of a gas in a measuring gas chamber, particularly for determining an oxygen concentration in an exhaust gas. The sensor element includes at least one first electrode and at least one second electrode, and at least one solid electrolyte connecting the first electrode and the second electrode. The second electrode is situated on the inside of the sensor element and is able to have gas from the measuring gas chamber applied to it via at least one gas access hole and at least one diffusion barrier. At least partially gas-impermeable cover layer is provided on the diffusion barrier, at least from area to area. The gas access hole has at least one chamfer in the vicinity of the cover layer.

14 Claims, 1 Drawing Sheet

SENSOR ELEMENT HAVING LIMITING CURRENT CALIBRATION FREE OF CRACKS

FIELD OF THE INVENTION

The present invention relates to sensor elements which are based on the electrolytic properties of certain solids, that is, on the solid capability of these solids to conduct specific ions.

BACKGROUND INFORMATION

Sensor elements of this kind are used, in particular, in the motor vehicle field to measure air-fuel gas mixture compositions. In this case, these sensor elements are also designated as “lambda probes”, and they play an important part in the reduction of pollutants in exhaust gases, both in Otto engines and in Diesel technology.

In the meantime, these types of sensor elements are understood to come in a variety of numerous specific embodiments. The exemplary embodiments and/or exemplary methods of the present invention is basically applicable to most of these known specific embodiments. A particular emphasis of the exemplary embodiments and/or exemplary methods of the present invention, to which the invention is not limited, however, is supposed to apply to so-called proportional probes or broadband probes, in which a gas mixture composition is determined, for example, via a current flowing through the solid electrolyte.

In many of such sensor elements, the calibration of the sensor elements after manufacturing plays an important part. This calibration is used, for instance, to adjust for production tolerances, and is performed for the purpose of setting rigidly specified electrical properties of the sensor elements.

One exemplary embodiment of such a calibratable sensor element which is able to be used within the scope of the exemplary embodiments and/or exemplary methods of the present invention, or modified according to the present invention, is discussed in DE 103 45 141 A1. This document refers to a sensor element in which a first electrode, lying outside, and a second electrode, lying inside, are separated by a solid electrolyte foil. The inner electrode is able to have gas from a measuring gas chamber applied to it, via a gas access hole. In order to reach the inner electrode, the gas has to penetrate a diffusion barrier in the process, via which a limiting current of the sensor element may be adjusted.

The diffusion barrier is at least locally closed by an at least extensively gas-tight cover layer. This cover layer, which may be produced, for instance, by printing a paste of zirconium oxide on the diffusion barrier, followed by a sintering step, may subsequently be locally cut open by specific laser cuts, so that a shortening of the diffusion path can be effected. The limiting current of the sensor element may be specifically adjusted by this shortening of the diffusion path. A base limiting current is produced in this instance by a frontally open input region of the diffusion barrier, which is able to be increased in a targeted manner by laser cuts.

The main challenge in such calibratable sensor elements, as in the sensor element of DE 103 45 141 A1, in which the calibration takes place by the local removal of a cover layer, lies in producing a cover layer that is free of cracks and is stable for a long time, in a calibration region above the diffusion barrier that is open to calibration. However, such a cover layer, that is crack-free and stable for a long time, assumes a good lamination between the diffusion barrier and the cover layer. This may usually be ensured by using a matched material/paste combination for the functional layers, as well as a controlled production process. Such lamination superstructures (layers) normally receive an additional pressure in a laminating process which, prior to a sintering step, further stabilizes the entire composite.

In the case of newer, linear diffusion barrier-electrode designs, that is, superstructures in which the diffusion barrier and the inner electrode are situated in a common inner layer, as in DE 103 45 141 A1, for instance, and in which an open gas access hole, which also functions as an adjustment hole, is present, this composite, when being laminated, is reinforced only partially by the laminating pressure. The electrode and the diffusion barrier are also situated in one plane in many radial designs, so that a similar problem arises. Whereas the cover layer-diffusion barrier region, lying below the solid electrolyte layer used as pump foil, on the contact terminal side, is exposed to a high laminating pressure, this is not so in the region of the gas access hole or the adjustment hole. Because of the nonhomogeneous laminating pressure on the sensor element in the vicinity of the bore hole edges, additional shear forces act which are able to destabilize this region even more, and are able to lead to stresses and cracks in the cover layer. Such stresses and cracks may, however, give rise to a lot of scrap and a great variation in the limiting current (from here on also designated as $I_p$) and in the k value.

The k value, in this context, is a measure for the pressure dependence of the limiting current, and is discussed in WO2007/104621, for example. The high variation of the limiting currents is compensated for again, as a rule, by the calibration, the laser calibration, for example. However, in this manner one is not able to compensate for the k value variation, as a rule. On the contrary, it may be established that the calibration also influences the k value, since during the calibration, the ratio between the gas phase diffusion and the Knudsen diffusion is changed. Because of this, the variation in the limiting currents acts on the variation in the k values in addition, via the calibration. In the case of a great variation in the limiting currents, the adjustments have to be of different sizes. The k value, in this instance, is also varied correspondingly differently because of the calibration.

The variation, particularly the variation of the k values, is further influenced by cavities which ensure the gas access to the diffusion barrier. These cavities are formed, for example, by the lower edge of the gas access hole and the solid electrolyte foil. This gas access hole to the diffusion barrier, that is able to be produced only with difficulty, makes an additional contribution to the variation in the limiting currents and the k values. This has a subordinate meaning for the limiting currents, since a limiting current may be adjusted subsequently. Different diffusion resistances in the input region, however, influence the k value decisively. If the proportion of the diffusion resistance over the diffusion barrier remains essentially stable, and if the proportion of the gas phase diffusion resistance of the overall diffusion resistance is changed by a narrowing in the cavity of the input region, the k value changes considerably. Because of the additional adjustment of the limiting currents, this influence will be reinforced under certain circumstances. In the usual designs, the k value may fluctuate in a range between 0.95 and 1.25 bar.

SUMMARY OF THE INVENTION

A sensor element and a method for producing a sensor element, particularly a sensor element according to the present invention, are therefore provided, which at least substantially avoid the abovementioned disadvantages of known methods and sensor elements, and which contribute to greatly reducing scrap and the variation in the k values. The exemplary embodiments and/or exemplary methods of the present invention starts out from a basic idea that, in order to avoid scrap and to minimize variations, cracks or gaps in the cover layer must absolutely be avoided. Besides that, a homogeneous, reproducible gas access to the diffusion barrier is decisive for the adjustment of k-value levels having a low variation.

The sensor element provided is used to determine at least one physical property of a gas in a measuring gas chamber. For instance, the determination of a gas mixture composition may be involved, for example, the determination of the concentration of a gas component that is to be identified. In particular, the exemplary embodiments and/or exemplary methods of the present invention may be used for determining an oxygen concentration, in the exhaust gas of internal combustion engines, for instance.

The sensor element includes at least one first electrode and at least one second electrode, as well as at least one solid electrolyte connecting the first electrode and the second electrode. The second electrode is situated on the inside of the sensor element and is able to have applied to it the gas from the measuring gas chamber, via at least one gas access hole and at least one diffusion barrier. An at least partially gas impermeable cover layer is provided on the diffusion barrier, at least from area to area. This being the case, we are able to refer to DE 103 45 141 for possible specific embodiments of the sensor element, for example.

One idea of the exemplary embodiments and/or exemplary methods of the present invention is to minimize the abovementioned problems, by suitable design of the gas access hole. For this purpose, it is proposed to provide the gas access hole, in the area of the cover, at least partially with a chamfer. In this connection, by chamfer one should understand a beveling of the edge of the gas access hole on the inside of the sensor element, which may be designed to be round or conical, for example. The gas access hole may open out onto the cover layer. In this case, the cover layer may be at least partially at a distance, in the vicinity of the gas access hole. The second electrode may be situated in at least one electrode cavity, the diffusion barrier being able to connect the electrode cavity to the gas access hole. Right from the start, the diffusion barrier may remain uncovered by the cover layer in at least one area, and thus make possible an unimpeded gas access to the diffusion barrier, in order to ensure a basic limiting current. As was described above, this basic limiting current may later be increased in a targeted manner, by additional laser cuts in the cover layer. The at least one uncovered area, that was present from the start, may be situated particularly in the vicinity of the chamfer, for instance in a cavity that is connected by the chamfer to the gas access hole, and thus to the measuring gas chamber.

The chamfer may be designed, in particular, as a conical chamfer, as was mentioned above. In this context, the chamfer may, for example, have an angle which may be within a range of 0° to 70°. The angle may be in the range of 20° and 70°. The chamfer angle $\alpha$, in this context, is defined as the angle that is developed between the side wall of the gas access hole, that may be designed to be cylindrical, and is developed outside the chamfer and within the chamfer region.

The sensor element may have a layer construction, for instance, a layer construction produced at least partially by a laminating method. This layer construction may include, for example, at least one first electrode layer having the at least one first electrode, the first electrode facing directly or indirectly towards the measuring gas chamber (for example, via a protective layer). Furthermore, the layer construction may have at least one solid electrolyte layer which includes the solid electrolyte mentioned. Furthermore, the layer construction may have at least one inner layer situated on the inside of the sensor element. By "on the inside" we mean a situation in which the inner layer is separated from the measuring gas chamber by at least one layer, the solid electrolyte layer that was mentioned, for instance. The inner layer includes the cover layer, the diffusion barrier and the second electrode. In this context, the cover layer is situated in the inner layer above the diffusion barrier, that is, as seen from the diffusion barrier, towards the measuring gas chamber. The gas access hole may connect the measuring gas chamber to the inner layer and, as described above, may open out on the cover layer, for example.

Moreover, a method for producing a sensor element is provided, particularly a sensor element according to the present invention. In this method, at least from area to area, an at least partially gas-impermeable cover layer is applied over the diffusion barrier. The gas access hole is chamfered in the area of this cover layer.

Furthermore, as described above, the cover layer may be partially removed for adjusting at least one sensor property of the sensor element, for instance, a limiting current and/or a k value. In principle, any desired method for removing the cover layer may be used, in this instance. If the removal of the cover layer may be performed using at least one laser ablation method, for instance, while irradiating the cover layer through the gas access hole, which is then being used simultaneously as an adjusting hole.

The chamfered gas access hole may be produced in a foil layer, before this foil layer is applied to the layer construction. In this context, a drill may particularly be used having at least one first, essentially cylindrically drilling drilling section, and under the rubric "essentially cylindrical," slightly conical shapes also being acceptable, for example, shapes having a cone angle of not more than 5°. In addition, the drill may include at least one second drill section that is essentially conical, for instance, having the abovementioned cone angle of the chamfer, which is in each case larger than a possibly present low cone angle of the first drill section. In this manner, for instance, one may produce gas access holes that are chamfered towards the middle of the sensor.

The provided sensor element and the provided method have a number of advantages compared to the known sensor elements and the known methods. Thus, especially shearing forces, that act on the cover layer/diffusion barrier lamination at the bore hole edge, may be considerably reduced. Because of this, the lamination becomes more stable and less susceptible to gaps and/or cracks. Based on this, scrap caused by too strong a deviation in the limiting currents is minimized, and the yield is increased. Furthermore, the k value is only influenced insubstantially, or not at all any more, by gaps and/or cracks, so that the k value variation may also be considerably reduced by this. In the usual sensor elements, however, gaps and cracks are the main parameters of influence on the variation of the k value. By lowering the variation of the limiting currents, the sensor elements are able to be calibrated more uniformly. Thus, the influence of the calibration on the k value is also essentially comparable for all sensor elements. The calibration leads to a uniform offset.

Moreover, the chamfering may also effect a more homogeneous, reproducible gas access to the diffusion barrier. The diffusion resistance, which is caused by a gas phase diffusion resistance in the front gas access or cavity, may hereby be set in a more reproducible manner. This is especially relevant in the abovementioned exemplary embodiment, in which the diffusion barrier remains right from the start uncovered by the cover layer in at least one area, this at least one area being situated in the vicinity of the chamfer. If the chamfer is sufficiently big, the influence of this cavity is minimized in the uncovered area or is completely excluded. The k value is then adjusted principally via the parameters, of the diffusion barrier and of the electrode cavity, that are able to be produced substantially more reproducibly, compared to this front cavity.

Exemplary embodiments of the present invention are depicted in the drawing and described in greater detail in the description below.

DETAILED DESCRIPTION

Figure 1:
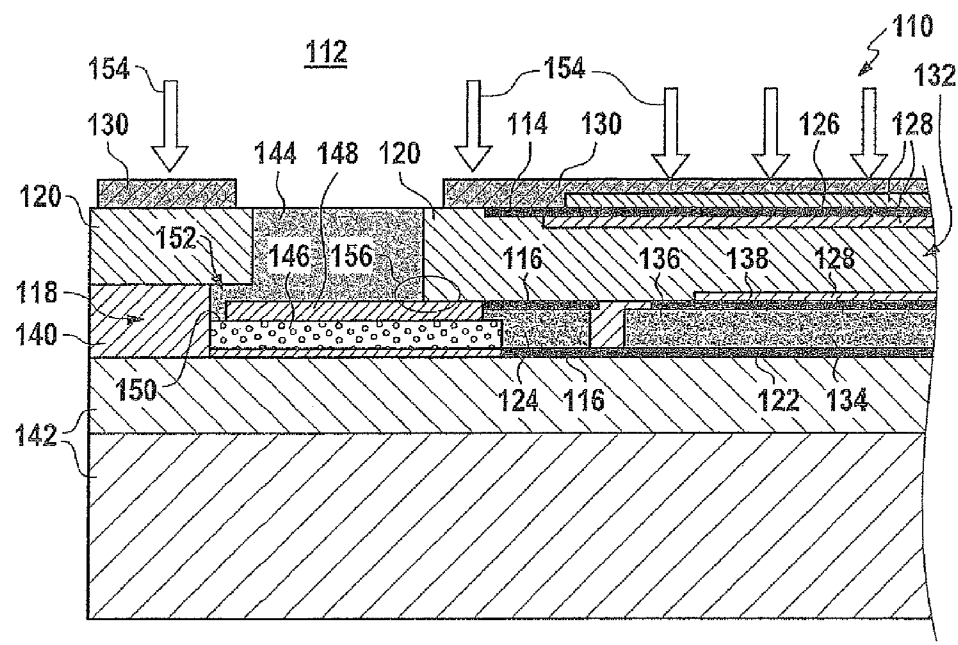
FIG. 1 shows an exemplary embodiment of a sensor element corresponding to the related art, in a sectional representation from the side.

FIG. 1 shows an exemplary embodiment of a sensor element 110, corresponding to the related art, in a sectional representation shown from the side. In this exemplary embodiment, sensor element 110 is used for determining the oxygen concentration and/or the partial oxygen concentration of an exhaust gas in a measuring gas chamber 112. In the figures, sensor element 110 is only shown schematically, and may have additional elements over and above the ones shown in the figures.

Sensor element 110 has a layer construction having a first electrode 114 which faces measuring gas chamber 112, and a second electrode 116 which is situated in an inner layer 118. First electrode 114 and second electrode 116 are separated by a solid electrolyte 120, which may include a zirconium dioxide foil, for example. Second electrode 116 is divided into two parts, is contacted via a second electrode supply line 122 and is essentially situated within an electrode cavity 124 that is accommodated within inner layer 118. Electrode cavity 124 may also be completely or partially filled with a gas-permeable, porous material.

First electrode 114 is contacted via an electrode supply line 126 that lies on the side of the layer construction of the sensor element 110 facing the measuring gas chamber 112, which may be electrically shielded from solid electrolyte 120 by an insulating layer 128. In the direction towards measuring gas chamber 112, first electrode 114 is protected by a protective layer 130. This protective layer 130 may have a gas-permeable porous material, for example, such as an aluminum oxide.

First electrode 114, solid electrolyte 120 and second electrode 116 together form a pump cell 132. Furthermore, sensor element 110 may also include a reference channel 134, which may, for example, be connected with outside air as a reference gas chamber. Reference channel 134 may be completely or partially filled with a porous material, for instance, also like electrode cavity 124, again with a porous aluminum oxide. Within reference channel 134, a reference electrode 136 may be situated, which is able to be electrically contacted via a reference electrode supply line 138. This reference electrode supply line 138 may again be electrically insulated from the solid electrolyte by an insulating layer 128. Using reference electrode 136, in common with solid electrolyte 120 and second electrode 116, one may draw a conclusion, from a potential difference, on the measuring gas composition in electrode cavity 124. The layer construction in FIG. 1 may also have additional cover layers 140, as well as substrate layers 142.

In order to apply gas from measuring gas chamber 112 to electrode cavity 124, a gas access hole 144 is provided in solid electrolyte layer 120 facing measuring gas chamber 112. A diffusion barrier 146 is accommodated in inner layer 118, below solid electrolyte layer 120. This diffusion barrier 146, which is situated in the vicinity of gas access hole 144, is covered by an essentially gas-impermeable cover layer 148, as is discussed, for instance, in DE 103 45 141 A1. The diffusion barrier may include a porous material of a metal oxide, for example, such as a zirconium oxide and/or an aluminum oxide. During the production of the layer construction, for example, cover layer 148 may also be produced by using, for instance, a zirconium oxide paste.

In a region of gas access hole 144, facing away from electrode cavity 124 in this exemplary embodiment, there remains an uncovered area 150 of diffusion barrier 146. In this uncovered area, a cavity 152 is formed within inner layer 118, which is connected to uncovered area 150, and which is open towards gas access hole 144. Cavity 152 or uncovered area 150 ensure that, even in the case shown in FIG. 1, in which no calibration has taken place yet, gas access is able to take place in the direction of diffusion barrier 146. From this uncovered area 150, the gas is able to diffuse through diffusion barrier 146 all the way into electrode cavity 124. The limiting current of sensor element 110 is then essentially determined by the combination of the gas phase diffusion resistance in the region of cavity 152, in which gas from gas access hole 144 has to flow to uncovered area 150, and the diffusion resistance inside solid of diffusion barrier 146.

As was described above, after the production of sensor element 110 a calibration of the sensor element is able to take place, in order to set a certain limiting current $I_p$ and/or a specified k value of sensor element 110, for example. For this purpose, cover layer 148 may be partially removed, for example, through gas access hole 144 (which is then simultaneously used as an adjustment hole) using a laser beam, in order to enlarge uncovered area 150 or to create new uncovered areas 150. In this manner, the path the gas has to cover inside diffusion barrier 146, in order to reach electrode cavity 124, is able to be shortened. Furthermore, diffusion barrier 146 itself may also be shortened using laser ablation. Both possibilities are described in DE 103 45 141 A1, for example.

With the aid of the layer construction shown in FIG. 1, which may be used as an example of a starting point for the present invention, the difficulties of this related art may be clarified. For instance, the layer construction shown in FIG. 1 may be produced by one or more laminating steps, combined, for example with one or more silk-screen printing steps. The laminating pressure is shown symbolically in FIG. 1 by reference numeral 154. In this connection, however, the above-mentioned difficulties may occur. A first difficulty is that cavity 152, which is connected upstream of diffusion barrier 146, as described above, is able to have a considerable influence on the diffusion resistance, and consequently on the k value. Based on fluctuations in the layer thicknesses of cover layer 148, diffusion barrier 146 and solid electrolyte 120, the gap that connects gas access hole 144 to cavity 152 may, however, be submitted to strong fluctuations. These difficulties of reproducibility may have a considerable effect on the variation in the k values.

A further difficulty may appear in the stress region designated by reference numeral 156 in FIG. 1, that is, at the transition between gas access hole 144 and cover layer 148, in the vicinity of electrode cavity 124. In this region, based on laminating pressure 154, that is transferred via solid electrolyte layer 120 to cover layer 148, strong stresses and shearing forces may appear, so that this region is particularly susceptible to the development of undesired gaps and/or cracks. The gaps or cracks may also considerably influence the k value and its variation.

Figure 2:
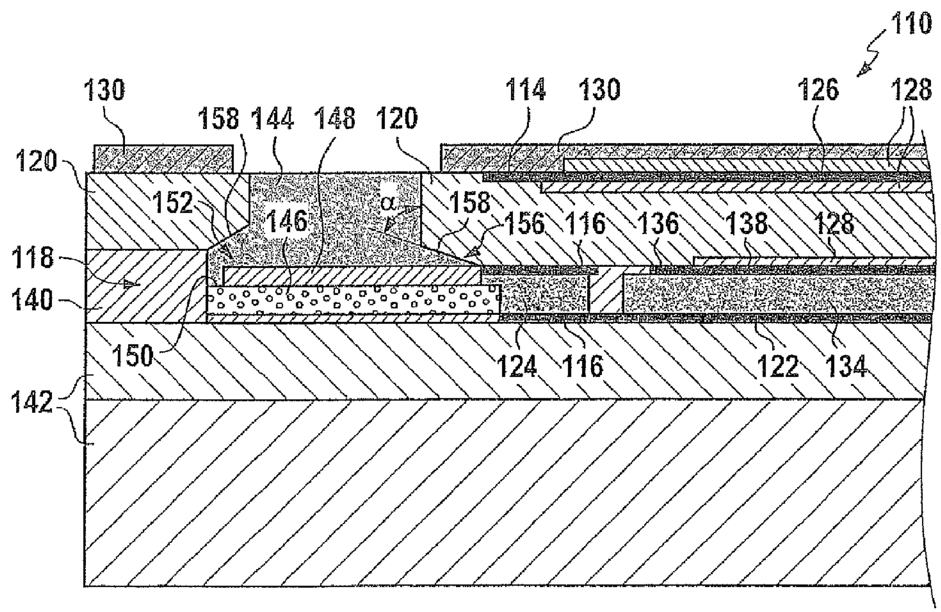
FIG. 2 shows an exemplary embodiment of a sensor element according to the present invention.

By contrast, in FIG. 2 an exemplary embodiment is shown of a sensor element 110 according to the exemplary embodiments and/or exemplary methods of the present invention, which avoids the problems mentioned, at least to a great extent. Sensor element 110, according to FIG. 2, first of all basically largely corresponds to the layer construction of the example according to FIG. 1. Accordingly, when it comes to describing the individual elements, we may largely refer to the above descriptions for FIG. 1. In contrast to the exemplary embodiment according to FIG. 1, sensor element 110 according to the present invention, according to FIG. 2, is, however, furnished with a chamfered gas access hole 144. Accordingly, gas access hole 144 has a chamfer 158 on its inside, that is, on its side facing inner layer 118. This chamfer is developed, in the exemplary embodiment shown in FIG. 2, on the one hand, in stress region 156, that is, at the transition between the wall of gas access hole 144 and cover layer 148 in the region of electrode cavity 124, and on the other hand, in the region of cavity 152 at the opposite end of cover layer 148. Chamfer 158 may have a chamfer angle such as $\alpha$, which may be close to 70°, for example.

This chamfer 158 is able to be introduced using a graded drill. This graded drill may include, for instance, a first drilling section having an essentially cylindrical shape, whose diameter is able to specify the actual size of gas access hole 144. This diameter may be within a range of 1 mm, for example. Furthermore, the drill may include at least one additional drilling section that is tapered or conical, and whose angle is adjusted to the drill diameter in such a way that a homogeneous chamfer is able to take place, without creating a bore hole edge having a larger bore hole diameter. Another manner of producing gas access hole 144 and chamfer 158 is also conceivable, however, such as a multistep drilling using different tools and/or drilling using a laser.

The effect of chamfer 158 is an improvement in the area of both the types of problem described above. For one thing, chamfer 158 acts in the region of cavity 152 so that the influence of this front cavity 152 or the gap between this cavity 152 and gas access hole 144 is greatly minimized or completely cut out. The k value may be set principally via the essentially reproducible parameters of the diffusion barrier (for instance, its layer thickness and/or its length) and electrode cavity 124.

For a second thing, chamfer 158 also has a favorable effect in (former) stress region 156. Since stresses, particularly shearing forces, are able to occur predominantly in the area of sharp, rectangular edges, such as in the rectangular transition between solid electrolyte 120 and cover layer 148, this stress in the region adjacent to electrode cavity 124 is greatly reduced by chamfer 158. Because of that, the laminate of diffusion barrier 146 and cover layer 148 becomes more stable and less susceptible to gaps and/or cracks, especially in this stress region 156. Thereby, the scrap produced, based on overly great fluctuations in the limiting current, is able be minimized. By lowering the variation of the limiting currents, sensor elements 110 are able to be calibrated more uniformly. Thus, the influence of the calibration on the k value is also essentially comparable for all sensor elements 110. The calibration leads to a uniform offset.

What is claimed is:

1. A sensor element for determining at least one physical property of a gas in a measuring gas chamber, comprising:

at least one first electrode;

at least one second electrode;

at least one solid electrolyte connecting the first electrode and the second electrode;

wherein the second electrode is situated on the inside of the sensor element and is able to have gas from the measuring gas chamber applied to it via at least one gas access hole and at least one diffusion barrier, an at least partially gas-impermeable cover layer being on the diffusion barrier, at least from area to area, and wherein the gas access hole has at least one chamfer in the vicinity of the cover layer.

2. The sensor element of claim 1, wherein the second electrode is situated in at least one electrode cavity, and the diffusion barrier connecting the electrode cavity to the gas access hole.

3. The sensor element of claim 1, wherein the gas access hole opens out on the cover layer.

4. The sensor element of claim 1, wherein the cover layer has been partially removed in the vicinity of the gas access hole.

5. The sensor element of claim 1, wherein the diffusion barrier is not covered by the cover layer in at least one area and enables an unimpeded gas access to the diffusion barrier, and wherein the at least one uncovered area is situated in the vicinity of the chamfer.

6. The sensor element of claim 1, wherein the chamfer has an angle $\alpha$, where $0° < \alpha \leq 70°$.

7. The sensor element of claim 1, wherein the sensor element has a layer construction having at least one first electrode layer, which includes the first electrode, the first electrode facing the measuring gas chamber, further having at least one solid electrolyte layer, the solid electrolyte layer including the solid electrolyte, and further having at least one inner layer situated on the inside of the sensor element, the inner layer including the cover layer, the diffusion barrier and the second electrode, the cover layer being situated in the inner layer above the diffusion barrier, and the gas access hole connecting the measuring gas chamber to the inner layer.

8. The sensor element of claim 1, wherein the sensor element is for determining an oxygen concentration in an exhaust gas.

9. The sensor element of claim 1, wherein the chamfer has an angle $\alpha$, where $20° \leq \alpha \leq 70°$.

10. A method for producing a sensor element, the method comprising:

applying gas from a measuring gas chamber to a second electrode, situated on the inside of the sensor element, via at least one gas access hole and at least one diffusion barrier;

applying at least a partially gas-impermeable cover layer onto the diffusion barrier, at least from area to area;

wherein the sensor element includes at least one first electrode and at least one second electrode, and at least one solid electrolyte connecting the first electrode and the second electrode, the second electrode being situated on the inside of the sensor element, and wherein the gas access hole is chamfered in the area of the cover layer.

11. The method of claim 10, wherein the sensor element has a layer construction, which is produced by a laminating process.

12. The method of claim 10, wherein the cover layer is partially removed for adjusting at least one sensor property of the sensor element, including adjusting at least one limiting current.

13. The method of claim 12, wherein a laser ablation process is used to remove the cover layer.

14. The method of claim 10, wherein the gas access hole is produced in a foil layer forming the solid electrolyte, a drill having at least one first, essentially cylindrical drilling section and at least one second essentially conical drilling section being used.

* * * * *